United States Patent [19]
Zeidler et al.

[11] 3,991,117
[45] Nov. 9, 1976

[54] PROCESS FOR THE PRODUCTION OF ALDEHYDES

[75] Inventors: Ulrich Zeidler, Dusseldorf-Benrath; Manfred Dohr, Dusseldorf-Holthausen; Herbert Lepper, Cologne-Mulheim, all of Germany

[73] Assignee: Henkel & Cie G.m.b.H., Dusseldorf-Holthausen, Germany

[22] Filed: June 4, 1971

[21] Appl. No.: 150,222

[30] Foreign Application Priority Data
June 6, 1970 Germany............................. 2027924

[52] U.S. Cl. .......................................... 260/603 HF
[51] Int. Cl.$^2$......................................... C07C 45/16
[58] Field of Search .................. 260/586 B, 603 HF

[56] References Cited
UNITED STATES PATENTS 2,051,266  8/1936  McAllister et al. ........... 260/603 HF
3,356,740  12/1967  Schneider....................... 260/617 F FOREIGN PATENTS OR APPLICATIONS
900,831  7/1962  United Kingdom .......... 260/603 HF
809,451  2/1959  United Kingdom .......... 260/603 HF

OTHER PUBLICATIONS

Aleksandrov et al., Chem. Abstracts, vol. 63, 4189a, 1965.

de Vries et al., Tetrahedron Letters, No. 54, pp. 5689–5690, 1968.

Primary Examiner—James O. Thomas, Jr.
Assistant Examiner—W. B. Lone
Attorney, Agent, or Firm—Hammond & Littell

[57] ABSTRACT

A process for the oxidative cleavage of vicinal diols having more than 2 carbon atoms in the presence of catalytic amounts of a heavy metal catalyst.

1 Claim, No Drawings

PROCESS FOR THE PRODUCTION OF ALDEHYDES

THE PRIOR ART

Splitting of vicinal diols by oxidation with formation of aldehydes, ketones or carboxylic acids has been known for a long time. Equivalent amounts of lead tetraacetate, sodium metaperiodate and other compounds with atoms in high stages of oxidation are used as oxidizing agents. Owing to the fact that equivalent amounts of oxidizing agents have to be used, such a method is economically uninteresting. It is also already known that vicinal diols can be oxidatively split by oxygen in the presence of certain heavy metal catalysts. This process, however, has only found use in the laboratory, which is due in particular to the fact that it has not previously been possible to carry out the reaction so that homogeneous reaction products are obtained. Moreover, several processes are known which, with use of different starting substances, allows the preparation of aldehydes in larger yields. Only recently have vicinal diols become specially interesting as raw materials, since they are obtainable in a relatively simple way from petrochemical raw materials, for example by hydroxylation of olefins. Such diols therefore offer the advantage, especially in the synthesis of higher aldehydes, that they can replace the fatty alcohols or fatty acids previously needed as raw materials. Other processes for the preparation of aldehydes which can start directly from petrochemical raw materials, for example the hydroformylation reaction, are known. However, a hydroformylation reaction as a method of synthesis of aldehydes has, on the one hand, the disadvantage that for the preparation of aldehydes of defined constitution, for example straight-chain aldehydes, α-olefines are used exclusively as raw materials, and, on the other hand, the hydroformylation reaction may take place on both carbon atoms of the double bond, that is that products are mostly formed which always contain more or less large amounts of branched-chain compounds formed by addition of CO in the 2-position. An aldehyde synthesis starting from diols, on the other hand, offers the possibility of the production of aldehydes with a foreseeable constitution and chain length in pure form.

OBJECTS OF THE INVENTION

An object of the invention is to satisfy the need existing on account of the above-described facts and to develop a process which, based on the known possibility of splitting vicinal diols with oxygen in the presence of catalysts, can be carried out on a commercial scale.

Another object of the present invention is the development of a process for the production of aldehydes having 2 to 9 carbon atoms which consists of contacting a vicinal diol having more than two carbon atoms with an oxygen-containing stream of gas in the presence of a catalytic amount of a heavy metal catalyst at a temperature of at least 40° C, which temperature is at least 50° C below the boiling point of said vicinal diol and not more than 50° C below the boiling point of the aldehyde formed at the pressure of the reaction, continuously distilling and removing the aldehyde and water formed with said stream of gas, and recovering said aldehyde having 2 to 9 carbon atoms.

These and other objects of the invention will become more apparent as the description thereof proceeds.

DESCRIPTION OF THE INVENTION

According to the invention, therefore, a vicinal diol having more than 2 carbon atoms is contacted with an oxygen-containing stream of gas in the presence of a catalytic amount of a heavy metal catalyst at a temperature of at least 40° C, which temperature is at least 50° C below the boiling point of the diol used and not more than 50° C below the boiling point of the aldehyde formed, and the aldehyde thus formed and the water produced in the reaction are distilled and removed from the reaction mixture on the gas stream as they are formed.

The process is applicable to terminal and nonterminal vicinal diols which may be both purely acyclic or may contain cycloalkyl or aryl groups. These diols may also be substituted if desired by hetero-atoms or hetero-atom groups, provided these are not themselves oxidizable under the reaction conditions. Preferably, the diols utilized have the formula

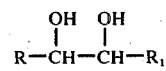

wherein R is a member selected from the group consisting of alkyl having from 1 to 8 carbon atoms and phenyl, $R_1$ is a member selected from the group consisting of hydrogen, alkyl having from 1 to 8 carbon atoms and phenyl, and R and $R_1$ together are butylene. Examples of diols utilizable as starting substances include: propanediol-1,2, butanediol-1,2, hexanediol-1,2, octanediol-2,3, octadecanediol-9,10, heptanediol-1,2, hexanediol-3,4, octanediol-1,2,-nonanediol-1,2, decanediol-1,2, octanediol-4,5, decanediol-5,6, dodecanediol-6,7, tetradecanediol-7,8, hexadecanediol-8,9, cyclohexanediol-1,2, 1,2-diphenyl-1,2,-dihydroxyethane, and phenyl-1,2-dihydroxyethane.

Preferably diols having 3 to 18 carbon atoms and especially purely aliphatic diols are used in the process of the invention.

These diols may be used singly or in admixture with one another, i.e., in particular the diol mixtures obtained by hydroxylation of certain olefin fractions may also be used.

Suitable catalysts are salts, oxides, sulfides and complex compounds of transition metals, which can occur in at least two different positive valency stages and which can be converted by oxygen into a higher valency state, as is the case, for example with manganese, cobalt, copper, cerium, vanadium and others.

The preferred catalysts are heavy metal compounds which are soluble in the reaction mixture, for example salts of the said metals with higher fatty acids, such as salts of lauric, myristic or palmitic acid.

The amount of catalyst employed can vary widely. Amounts of from 0.01% to 10% by weight, based on the diol, of the heavy metal compounds are customarily employed.

The oxidation gas used may be air or other oxygen-/inert gas mixtures. Preferably pure oxygen, i.e., oxygen of commercial quality, which does not contain more than 10% by volume of other gases, is used as the oxidation gas.

The oxidation gases should be brought in contact with the diol to be oxidized in as finely divided state as possible. This may be effected in a batch process by blowing in the gas through several fine jets at the bottom of the reaction vessel. A high-speed stirrer can also be introduced directly above the oxygen inlet at the bottom of the reaction vessel, or the stirrer itself may be provided with bores for the supply of oxidation gas. In a continuous operation it is advisable to pass the oxidation gas and diol to be reacted in countercurrent, and thus to provide the most intimate contact possible between the reactants, for example by use of spray columns or falling film columns. Another possibility for the development of a continuous process consists in spraying the catalyst-containing diol or diol mixture into a stream of oxygen.

When working in at high temperatures, and with relatively large amounts of reactants, it is advisable to preheat the oxidation gas to the temperature of the reaction mixture. The rate of introduction of the stream of oxidation gas is dependent upon several experimental parameters and therefore cannot be estimated in advance for all types of operation. For one thing it is governed by the type of diol used and the aldehyde formed, i.e., by the reactivity and the boiling temperature of these components; in addition it is governed by the type of apparatus, the type of gas feed and its distribution in the reaction mixture especially playing a part, and finally the amount of material to be reacted and whether the operation is continuous or discontinuous have to be taken into consideration in the choice of the rate of flow.

The oxidative splitting of the diols in the process according to the invention may be carried out in the absence of solvents. If, for any reason, it appears desirable to work in the presence of a solvent, for example in cases when the reaction is carried out at temperatures at which the vicinal diol to be reacted is solid, any solvents may be used which are inert towards oxygen under the reaction conditions and which are not too volatile at the operating temperature. Non-polar solvents such as paraffinic hydrocarbons and aromatics are suitable, and also polar solvents, which may be both aprotic and protonic are suitable.

Therefore, in contrast to the method known from Tetrahedron Letters 1968, page 5689, it has not been found necessary for a solvent to be present at all or for any solvent used to be polar and aprotic. Thus, the solvent does not directly influence the course of the reaction, as might be inferred from the said literature reference, but merely serves for the purpose of providing the reaction mixture with certain physical properties.

The reaction is generally carried out at atmospheric pressure. In some cases, especially in the preparation of high-boiling aldehydes, it may be of advantage to work under slightly reduced pressure.

The products are obtained in high yields and in great purity. Further working up of the aldehyde or mixture of aldehydes removed from the reaction mixture is generally not necessary.

It is regarded as surprising that no further oxidation to give carboxylic acids takes place during the removal of the aldehydes in the oxygen-containing gas stream. On the contrary, it was to be expected that high yields of aldehyde would only be attainable in a discontinuous process, in which first a partial oxidation followed by immediate removal of the aldehyde formed, as far as possible under an inert protective gas, is effected. Further, it was not to be expected that a solvent-free operation would lead to the desired result, since it is known from the said reference that the oxidative splitting of diols had to be carried out in the presence of very special solvents, i.e., aprotic polar solvents.

The products of the process serve as raw materials for various syntheses, especially as raw materials for polycondensation reactions with phenol or phenol derivatives. They may also be used as antioxidants; some of the aldehydes which can be produced by the process of the invention are also valuable aromatic substances.

The invention will be illustrated with reference to the following examples which are not limitative in any respect.

EXAMPLE 1

10 g of octanediol-2,3 and 0.7 g of cobaltous laurate were mixed and placed in a vessel provided with a frit as base plate and a descending condenser placed thereon. After heating the mixture to 180° C, a stream of oxygen was passed through the diol at a rate of 0.1 to 0.2 liters per minute. After an induction period of about 5 minutes, the aldehyde and the water formed in the reaction began to distill over. After about an hour the reaction was finished, 6 g (88%) of caproaldehyde being formed.

EXAMPLE 2

In the apparatus described in Example 1, 10 g of hexanediol-1,2 and 0.9 g of cobaltous laurate were mixed and heated with 10 g of octadecane to 160° C. After passing a stream of oxygen through at a rate of 0.15 liters per minute for 1 hour, the reaction was finished, and 6.4 g (88%) of valeraldehyde were distilled over.

EXAMPLE 3

In the apparatus described in Example 1, which was connected to a vacuum pump, 14.5 g of hexanediol-1,2 and 1.25 g of cobaltous laurate were heated to 90° C and a stream of oxygen at a total pressure of 400 Torr was passed through the mixture at a rate of 0.1 to 0.2 liters per minute. After 12 hours the reaction was finished, 8.2 g (77%) of valeraldehyde being formed.

EXAMPLE 4

In the apparatus described in Example 1, 10 g of d,1-octadecanediol-9,10 and 0.35 g of cobaltous laurate were heated to 190° C and a stream of oxygen at a rate of about 0.1 liter per minute was passed through the molten mixture for 30 minutes. 6.3 g (63%) of pelargonaldehyde were obtained.

EXAMPLE 5

In the apparatus described in Example 1, 10 g of octanediol-2,3 and 0.7 g of manganous laurate were mixed and heated to 160° C. After passing a stream of oxygen through the mixture at a rate of 0.1 liters per minute for half an hour, 2.5 g (36%) of caproaldehyde were distilled over.

EXAMPLE 6

In the apparatus described in Example 1, 10 g of a $C_{10}$ to $C_{14}$ diol mixture, prepared from a mixture of olefins with a central double bond, and 0.45 g of cobaltous laurate was heated to 180° C. After passing a stream of oxygen through at a rate of 0.15 liters per minute for a quarter of an hour, 8.3 g (83%) of a $C_5$ to $C_7$ aldehyde mixture were distilled over.

EXAMPLE 7

A similar result to that in Example 6 was obtained when a mixture of vicinal diols was oxidized in the presence of a cobaltous stearate catalyst. The mixture of vicinal diols was obtained by hydroxylation of an olefin mixture of chain length $C_{10}$ with a non-terminal double bond. Aldehydes of chain length of $C_2$ to $C_8$, corresponding to the position of the double bond in the starting olefin, were formed.

The advantages attainable with the invention are that aldehydes have been made accessible in a simple and economic way from the vicinal diols easily obtainable from petrochemical raw materials. A particular advantage of the process according to the invention is that the aldehydes obtained are of high purity, good yields are obtained and the use of solvents in the said process is not necessary.

The preceding specific embodiments are illustrative of the practice of the invention. It is to be understood, however, that other expedients known to those skilled in the art or disclosed herein may be practiced without departing from the spirit of the invention or the scope of the appended claims.

We claim:

1. A process for the production of aldehydes having 2 to 9 carbon atoms which consists of contacting a liquid phase of an aliphatic vicinal diol having more than two carbon atoms and at least one more carbon atom than said aldehyde and having the formula

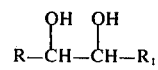

wherein R is alkyl having from 1 to 8 carbon atoms and $R_1$ is a member selected from the group consisting of hydrogen and alkyl having from 1 to 8 carbon atoms, with an oxygen-containing stream of gas in the presence of from 0.01% to 10% by weight, based on said vicinal diol, of a transition metal catalyst soluble in the reaction mixture selected from the group consisting of manganese, cobalt, copper, cerium and vanadium salts of higher fatty acids, in the absence of added solvents, at a temperature of at least 400° C, which temperature is at least 50° C below the boiling point of said vicinal diol and not more than 50° C below the boiling point of the aldehyde formed at the pressure of the reaction, continuously distilling and removing the aldehyde and water formed with said stream of gas, and recovering said aldehyde having 2 to 9 carbon atoms.

* * * * *